(12) United States Patent
Gorritxategi Arrondo et al.

(10) Patent No.: US 10,184,887 B2
(45) Date of Patent: Jan. 22, 2019

(54) FLUID MONITORING SYSTEM BASED ON NEAR-INFRARED SPECTROSCOPY

(71) Applicant: Atten2 Advanced Monitoring Technologies S.L.U., Eibar Gipuzkoa (ES)

(72) Inventors: Eneko Gorritxategi Arrondo, Eibar Gipuzkoa (ES); Jon Mabe Álvarez, Eibar Gipuzkoa (ES); Andoni Delgado Castrillo, Eibar Gipuzkoa (ES); Alberto Villar Verguizas, Eibar Gipuzkoa (ES); Harkaitz Urreta Prieto, Eibar Gipuzkoa (ES)

(73) Assignee: ATTEN2 ADVANCED MONITORING TECHNOLOGIES S.L.U., Eibar Gipuzkoa (ES)

( * ) Notice: Subject to any disclaimer, the term of this patent is extended or adjusted under 35 U.S.C. 154(b) by 87 days.

(21) Appl. No.: 15/368,094

(22) Filed: Dec. 2, 2016

(65) Prior Publication Data

US 2017/0160193 A1 Jun. 8, 2017

(30) Foreign Application Priority Data

Dec. 4, 2015 (EP) .................................... 15382609

(51) Int. Cl.
*G01N 21/35* (2014.01)
*G01N 21/3563* (2014.01)
(Continued)

(52) U.S. Cl.
CPC ......... *G01N 21/3563* (2013.01); *G01N 21/01* (2013.01); *G01N 21/359* (2013.01);
(Continued)

(58) Field of Classification Search
CPC .. G01N 21/3563; G01N 21/01; G01N 21/359; G01N 21/143; G01N 21/146
See application file for complete search history.

(56) References Cited

U.S. PATENT DOCUMENTS

| 5,905,570 A | * | 5/1999 | White | G01N 21/49 250/458.1 |
| 7,690,247 B1 | * | 4/2010 | Lapota | G01C 13/00 73/170.29 |

(Continued)

FOREIGN PATENT DOCUMENTS

| CN | 103234923 A | | 8/2013 | |
| JP | 2010261808 A | * | 11/2010 | |
| WO | WO 2014163615 A1 | * | 10/2014 | ......... G01N 33/1833 |

*Primary Examiner* — Michael C Bryant
(74) *Attorney, Agent, or Firm* — Cantor Colburn LLP (57) ABSTRACT

A system for monitoring at least one parameter of a fluid contained in a container includes a measuring device based on near-infrared spectroscopy designed to be submerged in the cited fluid to be monitored and to take measurements of the fluid. The measuring device includes a measuring area. The monitoring system includes a flotation system joined to the measuring device. The flotation system is arranged, during the use of the monitoring system, floating on the fluid to be monitored such that the measuring area of the measuring device is submerged in the fluid at a constant depth with respect to the level of fluid in the container, such that all the measurements taken by the measuring device are taken at the same depth with respect to the level of the fluid.

11 Claims, 4 Drawing Sheets

(51) Int. Cl.
*G01N 21/01* (2006.01)
*G01N 21/359* (2014.01)
*G01N 33/14* (2006.01)
*G01N 21/3577* (2014.01)
*G01N 21/85* (2006.01)

(52) U.S. Cl.
CPC ..... *G01N 21/3577* (2013.01); *G01N 21/8507* (2013.01); *G01N 33/143* (2013.01); *G01N 33/146* (2013.01); *G01N 2201/0212* (2013.01); *G01N 2201/0218* (2013.01); *G01N 2201/0231* (2013.01)

(56) References Cited

U.S. PATENT DOCUMENTS

| | | |
|---|---|---|
| 8,794,049 B1 | 8/2014 | Norkin et al. |
| 2002/0023849 A1 | 2/2002 | Vadgama et al. |
| 2010/0297291 A1 | 11/2010 | Shinoda et al. |

* cited by examiner

FLUID MONITORING SYSTEM BASED ON NEAR-INFRARED SPECTROSCOPY

CROSS REFERENCE TO RELATED APPLICATIONS

This application is related to and claims the benefit of European Patent Application No. 15382609.4, filed on Dec. 4, 2015, the contents of which are herein incorporated by reference in their entirety.

TECHNICAL FIELD

The present disclosure relates to monitoring and controlling fluids during the production process thereof. More specifically, the disclosure relates to monitoring the fermentation of foodstuffs, such as wines, both white and red, beers, juices, and tomatoes or dairy products, in order to obtain control over certain critical parameters during the process of fermentation and/or ageing based on the monitoring. The disclosure also relates to the integration of a container monitoring system for the continuous measuring of the fluid, at a constant height and ensuring the complete filling of the measuring cavity of the monitoring system.

BACKGROUND OF THE DISCLOSURE

The use of spectroscopy techniques for determining certain critical quality parameters in a fluid, for example wine, has been successful, but only when the analyte in question is elemental (potassium, calcium or iron). For example, U.S. Pat. No. 8,794,049B1 describes a system for the online monitoring of certain parameters of interest in the control of the wine fermentation process. In this case, the pressure created by the carbon dioxide flow which emanates as a result of the fermentation activity is monitored. In turn, patent application U.S. 2002/0023849A1 describes a method for detecting the ethanol presence in samples of a fluid using a non-porous PVC barrier without plasticizing interposed between the sample and an ethanol detector.

In recent years, near-infrared spectroscopy (NIRs) has been transformed into an alternative to traditional physical, chemical and chromatographic methods. For example, within the winegrowing sector, near-infrared technology (NIRs) allows the measuring of quality parameters of the wine required for the control of the fermentation processes. It is very useful to be able to carry out an automatic control for measuring the quality of the product and determining whether corrective intervention is necessary during the fermentation in order to maintain the quality. Furthermore, NIRs has the added advantage of being capable of quantifying multiple parameters at the same time using a single spectrum. The applications and measuring parameters for other sectors are also very varied from quality control of milk to the ripening percentage of fruits and vegetables. The spectral range of NIR extends from the highest wavelengths of the visible end (around 780 ηm) to 3000 ηm (13000 cm-1 to 3300 cm-1).

The advantages offered by NIRs technology are principally based on the speed of the processing and ease of use and handling, principally due to the scarce need to preprocess the analyte to be analyzed. In spite of the fact that a certain inversion in systems for online monitoring integrated into the production processes is involved, NIR spectroscopy has taken advantage over the rest of the analytic methods mainly due to the capacity thereof to carry out fast, non-destructive measurements both of solid compounds and liquids. However, compared with FTIR spectroscopy, NIR is characterized by its low specificity since in many cases the obtained bands are overlapping and have low sensitivity due to the fact that the large variations of the properties produce small variations in the visible NIR spectrum. Therefore the use of multivariate calibration techniques is necessary in order to be able to correlate the useful information of the spectrums obtained with the reference measurements obtained in the laboratory. Multivariate calibration is a discipline within chemiometry (a discipline which uses mathematical and statistical methods for designing and selecting optimal measuring and experimental procedures in order to provide the maximum amount of chemical information by means of the chemical data analysis) essential in NIR spectroscopy due to the complexity of the signal obtained by this technique. The objective of multivariate calibration is to search for the relation between a series of indirect measurements which are easy to obtain and a series of direct measurements from the laboratory which are expensive or require intensive labor. That is to say, to create a good calibration model such that the parameters measured in the laboratory by means of expensive techniques can be determined quantitatively in a fast and economic manner based on measurements carried out with cheaper methods.

The development of a multivariate calibration model is a complex process wherein the principal objective is to relate the N experimental variables (spectroscopy data) against one or various known properties of the samples. The typical strategy to be followed in the development of a multivariate calibration model consists of the following steps: selecting the sample group; determining the reference parameter; obtaining the analyte signal; processing the data; generating the calibration model; and validating.

On the other hand, the large number of spectral variables which are in the majority of the spectral data groups usually makes it difficult to predict a dependent variable. Furthermore, the existence of a large number of samples and variables means that the calibration process can be very costly in terms of time. It is therefore necessary nowadays to use the selection of predictor variables with the aim of not only saving time in the calibration, but also in order to eliminate those predictor variables (wavelength) which do not contain relevant information or which can damage the final result of the multivariate calibration. The exclusion of the irrelevant variables improves the characteristics of the model in terms of accuracy and robustness. In addition, the selection of variables is a very useful tool for improving the robustness of the multivariate calibration models. By means of the selection of variables it is possible to eliminate those variables which do not provide useful or relevant information, thereby obtaining an improved calibration model in terms of accuracy and robustness.

U.S. patent application U.S. 2010/0297291A1 describes an analysis method of the visible/near-infrared spectrum for monitoring certain parameters of the wine fermentation process. For this, laboratory measuring devices are used which are not integrated into the production process itself. Specifically, the method is developed on a grape sample.

In turn, Chinese patent application CN103234923 proposes an online monitoring method of the sugar content in a wine during fermentation by means of spectroscopy techniques.

SUMMARY

The present disclosure provides a measuring device and monitoring system based on near-infrared spectroscopy (NIRs) which allows the online monitoring of critical parameters in fluids to be implemented in a simple and quick manner. The system is especially useful within the agricultural sector although it can be applied to other sectors. With the present system, it is possible to determine various parameters, such as the degree of alcohol, acidity and sugars in the fermentation vats of wine or of other products, such as beers, juices, tomatoes and dairy products, amongst others, without the need to extract a sample from the fermentation vat. On the contrary, the sensing/measuring device is left introduced in the vat and the device takes measurements periodically (or upon request). By means of this new sensor system integrated into the container, measurements are carried out at a constant height, ensuring the complete filling of the cavity.

In a first aspect of the disclosure, a system for monitoring at least one parameter of a fluid contained in a container is provided, which comprises a measuring device based on near-infrared spectroscopy designed to be submerged in the cited fluid to be monitored and to take measurements of said fluid, wherein said measuring device comprises a measuring area. The monitoring system comprises a floatation system connected to said measuring device, said flotation system being arranged, during the use of the monitoring system, floating on the fluid to be monitored such that the measuring area of the measuring device is submerged in the fluid at a constant depth with respect to the level of fluid in the container, such that all the measurements taken by the measuring device are taken at the same depth with respect to the level of the fluid.

In one possible embodiment, the measuring device is connected to the flotation system by means of a bar with a specific length.

In one possible embodiment, the flotation system comprises connection means configured for connecting the flotation system to the exterior of the device.

In one possible embodiment, the measuring device is configured for taking measurements of the fluid periodically or randomly.

In one possible embodiment, the measuring device comprises a light source which works in the visible light and near infrared spectrum and a detection system based on near-infrared spectroscopy, wherein said light source is configured for illuminating the fluid to be monitored and said detection system is configured for taking at least one measurement of the light spectrum which passes through said fluid to be monitored. The measuring device preferably comprises means for recording the temperature of the fluid to be monitored, means for recording the temperature of the detection system and means for recording the temperature of the light source. Also preferably, the measuring device comprises processing means configured for processing the measurements taken by the detection system and by the three means for recording the temperature of the fluid, of the detection system and of the light source.

In one preferred embodiment, the monitoring system also comprises a positioning system configured for rotating the measuring device in the interior of the fluid such that the measuring area is arranged in the interior of the fluid with the opening thereof facing upwards.

Preferably, the positioning system comprises an opening and closing mechanism formed by a first piece and a second piece articulated to each other by means of a common axis, and a cable, wherein the first piece is fixed to the measuring device and the second piece is fixed to the bar, said positioning system being configured for, once the assembly formed by the bar and the measuring device, joined by said opening and closing mechanism forming an angle of 90°, is introduced in the container full of fluid, pulling the cable from the exterior of the container until the opening and closing mechanism is folded forming an angle of 0° between said first and second pieces, the cavity being arranged in a vertical position, facilitating the release of air bubbles.

In one particular embodiment, the positioning system also comprises a clamping system for the cable configured for fixing the position of the same following the rotation of the measuring device and maintaining the groove in the vertical position during the sampling time.

In one possible embodiment, the fluid, at least one parameter of which one wishes to monitor, is a wine and the at least one parameter to be monitored is one of the following: the degree of alcohol, the degree of acidity or the degree of sugars present in the wine.

The advantages of the disclosure are apparent in view of the description which is presented below.

BRIEF DESCRIPTION OF THE DRAWINGS

In order to complement the description and with the aim of aiding a better understanding of the characteristics of the disclosure, in accordance with a practical exemplary embodiment of the same, a set of figures is enclosed as an integral part of the description, in which the following is depicted in an illustrative and non-limiting manner.

DETAILED DESCRIPTION OF THE DRAWINGS

In this text, the word "comprises" and the variants thereof (such as "comprising", etc.) should not be interpreted in an exclusionary manner, that is to say, they do not exclude the possibility of what has been described including other elements, steps etc.

In the context of the present disclosure, the term "approximately" and the terms in the family thereof (such as "approximate", etc.) should be understood as indicative values very close to those which accompany the term previously mentioned. That is to say, a deviation within the acceptable limits based on an exact value should be accepted since the person skilled in the art understands that said deviation based on the indicative values is inevitable due to the inaccuracies of the measurement, etc. The same applies to the terms "around" and "substantially".

The monitoring system of the disclosure comprises a measuring device 10 designed to be integrated into a container. The measuring device 10 is a near-infrared spectroscopy (NIRs) device and is designed to be introduced into the fermentation vat of the fluid which is being produced (for example wine) and left introduced in the vat during the fermentation process. In this way, the measuring device 10 can take measurements of various parameters which affect the fermentation process without the need to extract a fluid sample from the vat. By correctly interpreting the values taken by the measurement parameters, an action can be performed on the fluid in question or decisions can be taken based, for example, on the degree of ripeness thereof. The device 10 can take measurements periodically or non-periodically (for example upon request). The measurements are taken at a constant height, also ensuring the complete filling of the cavity (measuring area) in which the measurements are taken. The fluid collected in the vat is preferably a liquid. Non-limiting examples of liquids, the fermentation or ageing process of which can be monitored with the measuring device 10 are wines, beers, juices, tomato or dairy products, such as milk, yogurts, etc. The parameters of these products which can be monitored are, for example, in a non-limiting manner, the degree of alcohol, acidity or sugars.

Figure 1:
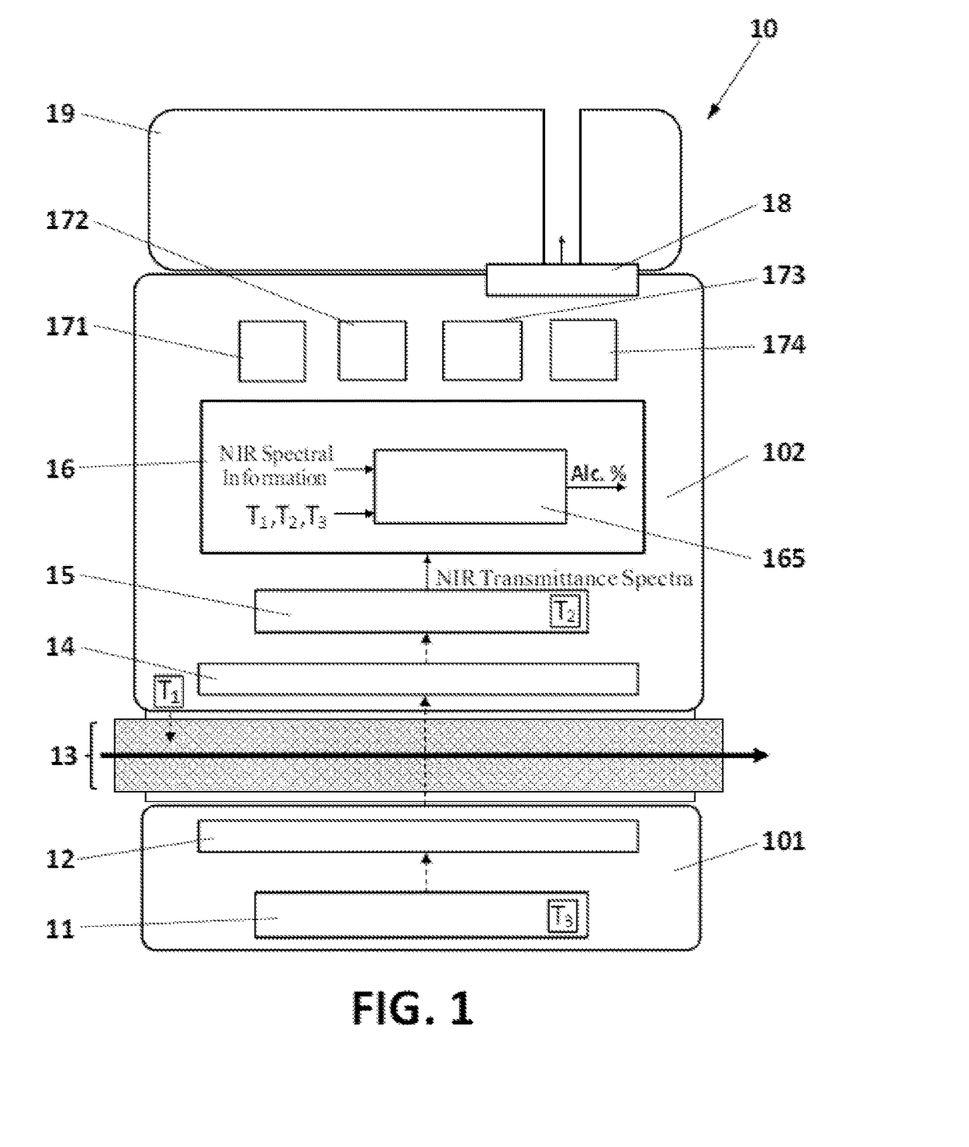
FIG. 1 shows a block diagram of a NIRs measuring device in accordance with one possible embodiment of the disclosure. The block diagram illustrates the functioning of the measuring device.

FIG. 1 shows a block diagram or functional diagram of the measuring device 10. The measurement or measurements is/are taken by arranging the analyte/fluid to be measured between a light system (NIR light source) 11 and a detection system (NIR spectroscopy) 15 such as is described below. Both systems (light and detection) are sealed by means of two protection windows 12 14 transparent in the working range (NIR). Moreover, the temperature of the fluid to be measured, the temperature of the light system and the temperature of the spectroscopy system (detection system) which collects the signal are monitored. The chemiometric algorithms are integrated in the system itself and carry out the calculation of the variables of interest based on the detected spectrum in order to control the state of the analyte/fluid which is analyzed.

The measuring device 10, of which a block diagram is shown in FIG. 1, has a series of optoelectronic elements integrated into a casing, sheath or encapsulation. FIG. 1 shows a diagram of a cut of this encapsulation, which allows the interior thereof to be seen in a schematic manner. The casing, sheath or encapsulation has a shape which allows the passage of the fluid between two external walls of the device. That is to say, the fluid passes through an area 13 exterior to the device 10. This area 13 is a type of tunnel or conduit between the exterior surface of a part 101 of the device and the exterior surface of another part 102 of the device. That is to say, as is observed in FIGS. 2 and 3, the sheath has a determined thickness in the lower part or portion 101 and in the upper part or portion 102, and experiences a narrowing 103 in an intermediate part or portion between the lower 101 and upper 102 parts (narrowing 103 which is observed in FIGS. 2 and 3) such that the sheath is divided into an upper part 102 and a lower part 101, joined by a narrow part 103 of the sheath, leaving a hollow 13 through which the fluid flows when the device 10 has been inserted or submerged in the fluid under supervision. In the lower part 101 with respect to the narrow area 103, that is to say, in the part intended to remain submerged to the greatest extent in the fluid, that is to say, in the part opposite to the end through which the device 10 is held or connected from the exterior of the vat or container 30, the device 10 has a light source (light system) 11. The wall of the lower part 101 in contact with the fluid sample (which passes through the channel or tunnel 13) is hermetically sealed by a transparent protection window 12 (transparent to the working wavelength). The light source 11 is a light source in the visible and infrared (VIS+IR) light spectrum. Preferably it is a wide-band light source, for example, but in a non-limiting manner, a halogen lamp which provides a stable spectrum from the ultraviolet to the far- or deep-infrared. The light source 11 is at a determined temperature $T_3$ recorded by a temperature sensor arranged close to the light source 11. The light source 11 is orientated towards the area 13 through which the fluid flows. The transparent protection window 12 is situated between the light source 11 and the area 13 through which the fluid flows. In one possible, non-limiting embodiment, this transparent protection window 12 is implemented in quartz. The light emitted by the light source 11 travels through this transparent window 12 to the fluid which is in the hollow 13.

On the other side of the fluid under supervision, that is to say, on the upper part 101 of the casing or sheath, the device 10 has another transparent protection window 14 similar to the window 12 of the lower part 102. As the dotted arrows in FIG. 1 show, the light, which comes from the source 11, passes through the first transparent window 12 and through the fluid which circulates through the area 13 which is between the lower 101 and upper 102 part of the casing, continues travelling and also passes through the transparent window 14 until it arrives at a detection system 15. The detection system is a NIR spectrometer 15. The NIR spectrometer 15 is a device with which a transmittance signal is obtained in the NIR range. The spectrometer 15 is at a temperature $T_2$, recorded by a temperature sensor arranged close to the spectrometer 15. In turn, a third temperature sensor records the temperature $T_1$ of the sample fluid. This sensor is situated in proximity to the sample fluid, preferably in the upper part 102 of the sheath. In the diagram in FIG. 1, the temperature sensor which records the temperature $T_1$ of the sample fluid is situated in the upper part 102 of the sheath. In one possible embodiment, the temperature sensors which measure the temperatures $T_1$, $T_2$ and $T_3$ are thermocouples.

It is necessary to control the temperatures of the fluid and of the light and detection systems because the measurements taken by the NIR spectrometer 15 fluctuate with the temperature and temperature can experience very pronounced changes. In fact, the influence of the temperature affects the signal obtained in two different ways. Firstly, if the temperature $T_3$ of the emitter 11 and/or the temperature $T_2$ of the detector 15 changes, the measurement taken of the sample (considering that the sample does not vary), varies with respect to the measurement which would be taken if said temperatures $T_2$ $T_3$ were not altered. If the temperature $T_3$ of the light emitter 11 varies, the amount of light which the emitter 11 emits, can vary up to 50%. Something similar occurs if the temperature $T_2$ of the receiver or NIR spectrometer 15 varies. In order to minimize the impact of these temperature variations, the device 10 has a system integrated, not depicted, for carrying out the measurements at a nominal temperature. The second key aspect in relation to the temperature is that temperature changes $T_1$ of the sample itself can alter the signal, since the formulation of the analyte itself, which is being analyzed, changes. That is to say, the temperature at which the measurements have been taken should be taken into account in order to correctly interpret the parameters under analysis. This is especially relevant in the specific case of the wine fermentation vats, in which the temperature can go from 2/3° C. to 40/42° C.

The upper part 102 of the sheath, that is to say, the part that houses the NIR spectrometer 15 also comprises processing means 16 for processing the measurements taken by the NIR spectrometer 15 and by the three temperature sensors (for controlling the emitter, receiver and analyte). This part 102 is referred to as the "upper part" because it is the part which, during the immersion of the device 10 in the fluid collected in a container, remains closest to the cable or rope 31 41 which joins the device 10 to the exterior of the container (see for example FIGS. 2 and 3). However, in the embodiments of FIGS. 4 and 5, it is observed that during the use of the monitoring system, the part called "upper part" does not always necessarily remain closest to the upper end of the container. The same is applicable, but the other way round, for the term "lower part". In one possible embodiment, the processing means 16 are an embedded microcontroller, but any processor, microprocessor or hardware device housing the software necessary for carrying out the control and processing tasks for the recorded information can be used. The processing means 16 houses the chemiometric algorithms 165, implemented by means of software, which carry out the calculation of the variable of interest based on the NIR spectral information recorded by the spectrometer 15 and of the temperatures of the fluid to be measured $T_1$, the temperature of the light system $T_3$ and the temperatures of the spectrometer system $T_2$ which collects the signal. These algorithms are out of the scope of the disclosure. In the particular case in which the fluid is a wine fermented in a vat, the variables of interest, which are calculated based on the spectrum detected and on the temperature recorded, are: the degree of alcohol and the content of sugars to monitor the fermentation process of the wine.

The upper part 102 of the sheath can incorporate some additional elements, such as a temperature sensor 171 to control the temperature of the electronic system, a power source or battery 172, information storage means 173, such as for example a memory and communications electronics 174 for the exchange of information with other devices or between components of the device itself, for example to control the powering on of the light source 11 and the time for which it remains powered on.

Lastly, the device 10 includes, preferably in the upper part 102, and more preferably at the end of the same opposed to the end at which the first transparent sheet 12 is located, a connector or connection interface 18. This interface 18 is used for the exchange of control information, communications and power. The part of the device 10 where this interface 18 is located is preferable protected by a protective ring 19, preferably made of plastic or any other material which forms a seal to avoid air entering into contact with the sample which is being analyzed.

Below, two embodiments of measuring systems integrated into a container are described, based on a measuring device 10 like the one described in this text.

The manner of filling the vats, containers or recipients for storing the fluid implies that the fill level is frequently different from one vat to the other. Moreover, the level of fluid in the vat can vary during the fermentation process, ageing or treatment process which is involved. The inventors have observed that it is interesting to carry out measurements at the same height (depth), taking as a reference for example the maximum fill level, since the conditions can change as a function of the height at which the measurement is carried out. In the specific case of wine, during the fermentation and ageing process thereof, one of the key aspects is the turbidity of the wine. The turbidity indicates the amount of solid particles suspended in the fluid and this turbidity can vary significantly at different heights, since the generation of $CO_2$ during the fermentation means that these solid particles move upwards. That is to say, it has been observed that the depth with respect to the level of fluid in the container, at which the measurements are taken, conditions the result of the measurements. In order to solve this problem, a system has been developed for maintaining the measuring device 10 at the same relative distance with respect to the fill level of the vat or storage container at all times. The height regulating system allows the measuring device 10 to be anchored at a fixed distance with respect to the fill level, thereby solving the problem detected.

Figure 2:
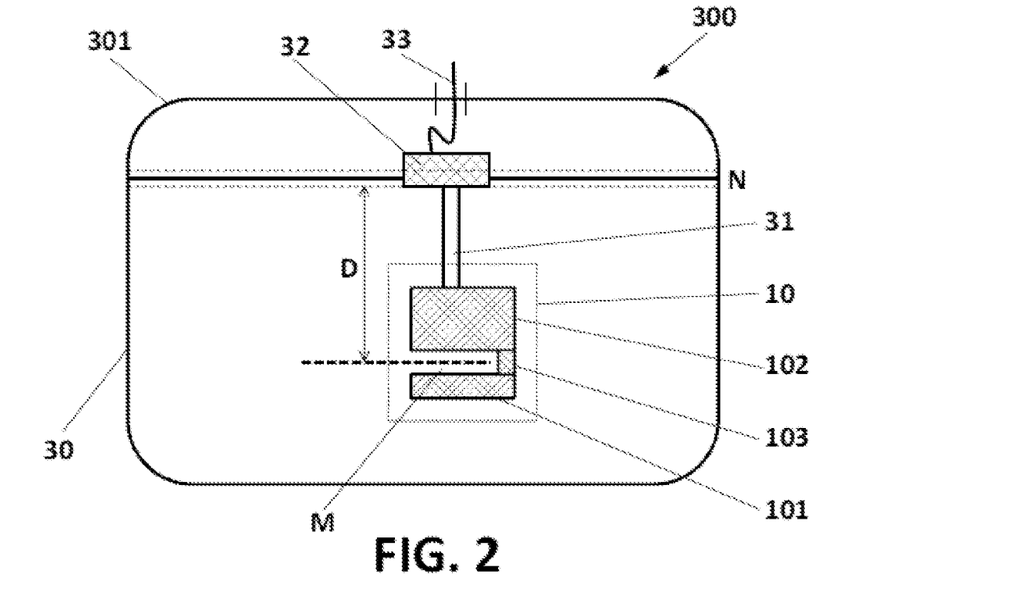
FIG. 2 shows a diagram of a monitoring system integrated into a container in accordance with a first embodiment of the disclosure. The monitoring system comprises a measuring device like the one depicted in FIG. 1.

FIG. 2 shows a diagram of a monitoring system 300 integrated into a container 30 in accordance with a first embodiment of the disclosure. The height regulation is achieved by means of a flotation system 32. The flotation system 32 is preferably an element, preferably a cylinder, made of a material floating in the fluid or liquid under supervision. A non-limiting example of such a material is cork. The flotation system 32 is situated floating on the level of the fluid within the vat, tank or container 30. The measuring device 10 is joined or connected to the flotation system 32 by means of a bar 31 with a specific length (selected as a function of the dimensions of the container 30, of the product to be monitored, etc.) such that the measuring device 10 is submerged in the fluid at a depth determined by the length of the bar 31. The flotation system 32 can be controlled from the exterior of the container 30 by means of connection means 33 which can take the form, for example, of a rope or cable 33 connected to the flotation system 32 at one end. Alternatively, this first end of the rope or cable 33 does not end in the flotation system 32, but once hooked to the flotation system 32, it is introduced into the interior of the bar 31, along the same, or runs parallel to the bar 31. The other end of the rope or cable 33 is arranged on the exterior of the vat or container for handling from the exterior of the measuring system 300. Preferably the cable 33 is also a communications cable to cause the result of the measurements and subsequent processing to arrive towards the exterior of the vat. Alternatively, the cable 33 is a conventional mechanical cable and together with the same, in parallel or in the interior thereof, a communications cable is located for the transport of the mentioned data to the exterior. The vat or container 30 is preferably closed/sealed by means of a cover 301, for example made of plastic, so that the content thereof does not enter into contact with the exterior air. The rope or cable 33 which connects the floatation system 32 to the exterior of the vat passes through the cover which closes the container through a hole or groove designed for such purpose.

FIG. 2 shows the measuring area M (13 in FIG. 1) and the distance D between the measuring area M and the maximum fill level of the container 30. In FIG. 2, the fill level N is also shown with a thick line and around this fill level N, the possible level changes are shown, with both dotted lines. These possible level changes indicate the level changes which may occur in the fermentation and ageing process of the fluid, for example wine. In this way, thanks to the flotation system 32, a monitoring system, auto-regulatable in height, is achieved. It is thereby guaranteed that all the measurements regarding the fluid are taken at the depth of interest (D). The bar 31 contains the cable 33 (or mechanical cable and communications cable). The communications cable is used to extract the data from the sensor 10. Said communications cable is connected to the communications and power interface 18. The monitoring system 300 of this embodiment is especially advantageous for monitoring fluids, in the processes of which a significant variation of the level of the fluid in the vat can be produced (for example because due to the fermentation process the amount of product in the production process significantly varies). In these cases, the flotation system 32 maintains the measuring device 10 at the same level with respect to the height or level of fluid N, irrespective of whether a change in the total level of the fluid in the container occurs. Alternatively to the sending of the information to the exterior by means of the communications cable, this sending can be carried out wirelessly depending on the acquisition system present in the plant.

Figure 3:
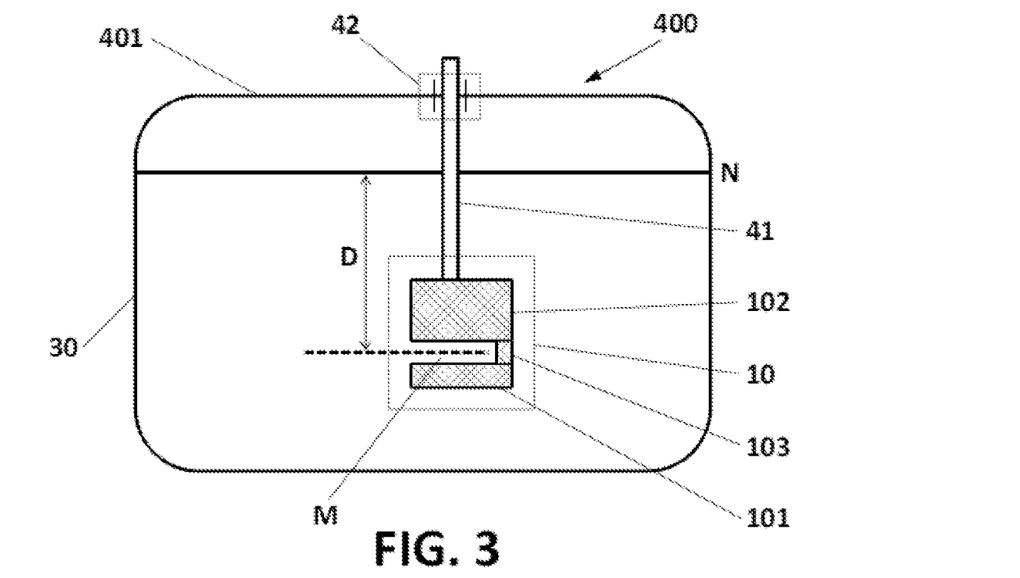
FIG. 3 shows a diagram of another monitoring system integrated into a container in accordance with a second embodiment of the disclosure. The monitoring system comprises a measuring device like the one depicted in FIG. 1.

FIG. 3 shows a diagram of another monitoring system 400 integrated into a container 30 in accordance with a second embodiment of the disclosure. The monitoring system 400 comprises a measuring device 10 like those illustrated in FIGS. 1 and 2. The measuring system 400 comprises a height regulation system 42 configured so that the measuring device 10 submerged in the fluid always maintains the same distance (depth) with respect to the maximum level of fluid N. The height regulation system 42 comprises an anchor which, by unscrewing it, allows it to be regulated/moved in terms of height and once screwed, remains fixed at a specific height. FIG. 3 shows the measuring area M (13 in FIG. 1) of the measuring device 10 and the distance D between the measuring area M and the fill level N of the container 30. The height regulation system 42 is situated at a certain height above the maximum level of fluid N. In one preferred embodiment, in which the vat, tank or container 30 is provided with a cover 401 for the closing thereof, the height regulation system 42 is coupled to or inserted in the cover 401. The measuring device 10 is joined or connected to the height regulation system 42 by means of a cable or rope 41 which can be deployed or collected in the height regulation system 42 as a function of the variations of the fill level N of the fluid in the vat. Thus, as in the previous embodiment, the measuring device 10 is submerged in the fluid at a depth determined by the length of the cable or rope 41 which, in this case is controlled by the height regulation system 42. The height regulation system 42 is controlled from the exterior of the container 30. In this way, thanks to the height regulation system 42, it is guaranteed that all the measurements regarding the fluid are taken at the depth of interest. The measurements taken are sent to the exterior as in the embodiment of FIG. 2, that is to say, either by way of a cable or wirelessly.

The inventors have observed that one important aspect in order to carry out the correct measurement is that the measuring groove or cavity (13 in FIG. 1, M in FIGS. 2 and 3) is completely filled with the liquid to be measured. On the other hand, the measuring device 10 should be introduced into the vat or container 30 as is illustrated in FIGS. 1 to 3, since the cover 301 401 of the vat normally has a very small diameter, which only allows the insertion of the device 10 such that the measuring cavity 13, M is in the horizontal position. By situating the groove or cavity 13, M horizontally (as is shown in FIGS. 2 and 3), it can cause the cavity not to fill completely, since occasionally this horizontal arrangement implies that not all the air (undesired bubbles in the measurements) exits from the groove. The system of the disclosure overcomes this previous drawback as is explained below.

Figure 4A:
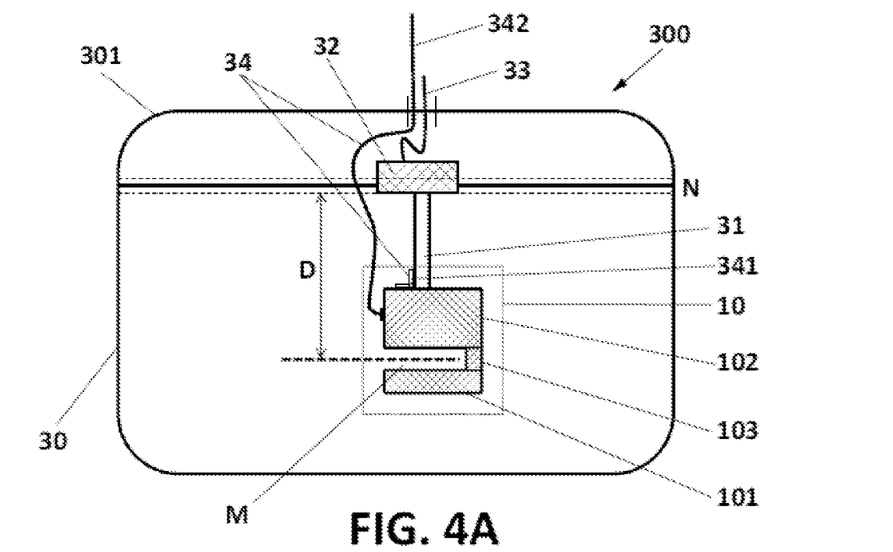
FIGS. 4A and 4B show a monitoring system in accordance with a possible embodiment of the disclosure, which includes a mechanical system which allows the measuring device to be rotated and to leave the cavity in perpendicular way in order to obtain suitable filling which avoids the presence of air bubbles in the measuring area.
Figure 4B:
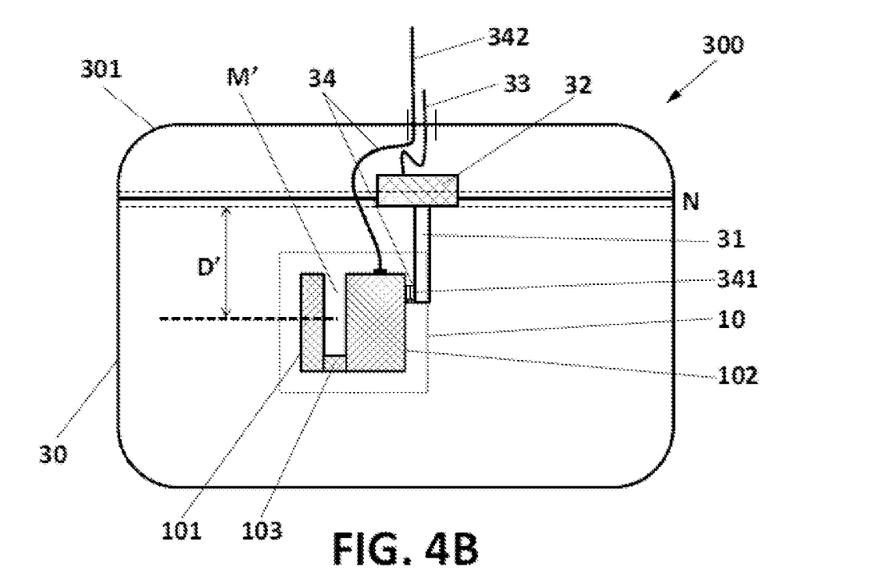
Figure 5A:
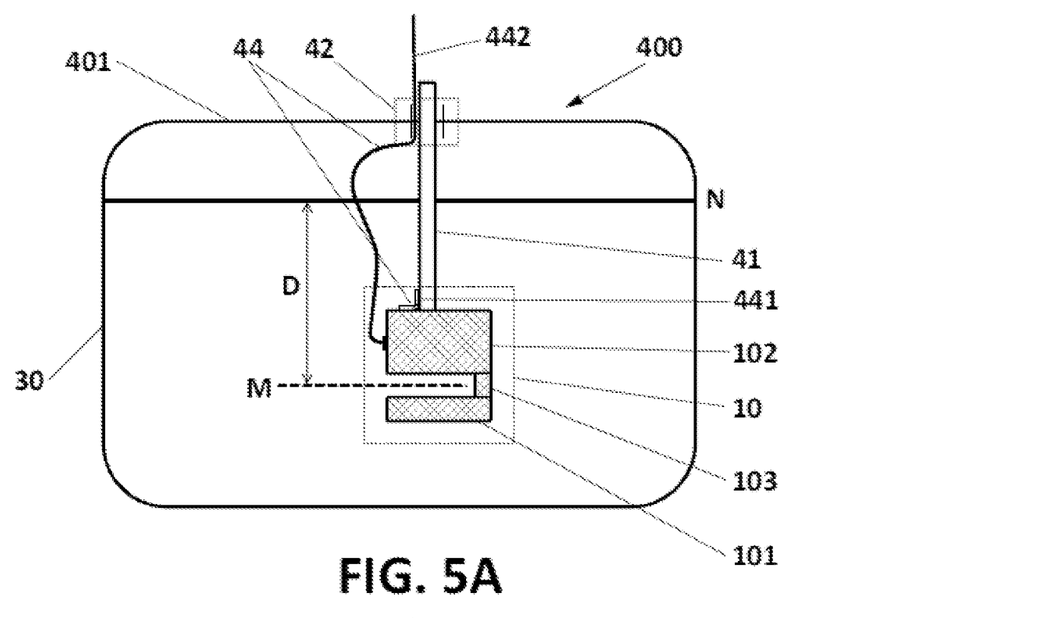
FIGS. 5A and 5B show a monitoring system which includes a mechanical system in accordance with another embodiment of the disclosure.
Figure 5B:
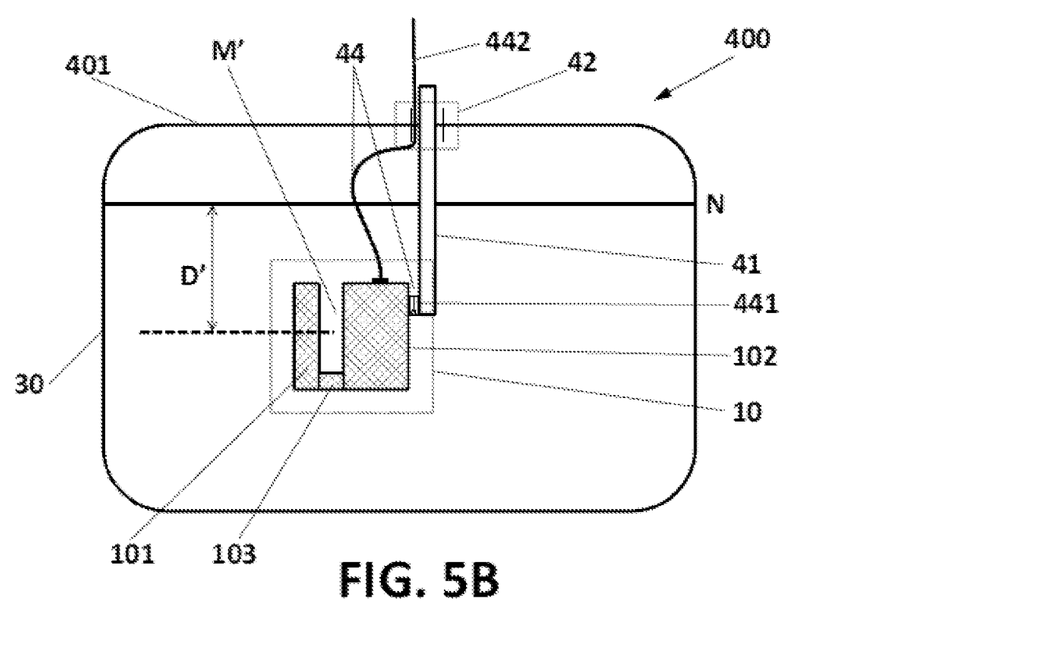

FIGS. 4A and 4B show a particular embodiment of the monitoring system 300 of FIG. 2, in which a positioning system 34 is incorporated to facilitate the filling of the measuring area M, M'. FIGS. 5A and 5B show a particular embodiment of the monitoring system 400 of FIG. 3, in which a positioning system 44 is incorporated. The mechanical system (positioning system) 34 44 allows the measuring device 10 to rotate in order to orientate the groove M, M' in a vertical arrangement, thereby facilitating the exit of air and facilitating the filling of the groove or cavity M' with the liquid or analyte to be measured. It should be noted that the cavity or groove has been referenced as M when it is situated horizontally (FIGS. 4A and 5A) and as M' when it has been rotated and is arranged vertically (FIGS. 4B and 5B), but, in reality the cavity delimited by the walls 101 102 103 of the device 10 does not vary with the rotation of the same. That is to say, the positioning system, 34 44 allows the measuring device 10 to rotate 90° and leave the measuring cavity or area M' perpendicular to the original position thereof (that is to say with the opening facing upwards) in order to obtain suitable filling which avoids the presence of air bubbles in the measuring area. This position facilitates the removal of air bubbles which can exit the cavity naturally, ascending vertically towards the open area of the cavity.

A possible embodiment of a positioning system 34 44 is described below. The sheath or casing of the measuring device 10 comprises an opening and closing mechanism 341 formed by two pieces articulated by a common axis. One of the pieces is fixed to the sheath or casing of the device 10 and the other piece is fixed to the bar 31 on the part of the same which remains next to the sheath or casing. In one possible embodiment, the opening and closing mechanism 341 is a hinge. The mechanism 341 is designed so that the maximum opening thereof is 90° as is illustrated in FIG. 4A. Moreover, the sheath or casing has incorporated on the exterior thereof a cable 342, for example on the same wall on which the first piece of the opening and closing mechanism 341 is located or, as is shown in FIG. 4A, on a wall perpendicular to the wall on which the first piece of the opening and closing mechanism 341 is located. The functioning of the positioning system 34 is the following: once the assembly formed by the bar 31 and the measuring device 10, joined by the opening and closing mechanism 341 arranged forming an angle of 90°, is introduced in the container 30 filled with fluid until the measuring device 10 is completely submerged in the interior of the fluid, the cable 342, the free end of which should emerge through the cover 301 of the container, is pulled from the exterior of the container, until the opening and closing mechanism 341 is deployed or closed, forming an angle of 0° between the two pieces which form it. This final position following the manipulation of the positioning system 341 is shown in FIG. 4B. As the second piece of the mechanism 341 is joined to the sheath or casing, upon pulling the cable 342 upwards, the mechanism 341, upon being closed approximating the first piece (joined to the bar 31), causes the sheath or casing to rotate until, in the completely closed position thereof, the cavity M' is arranged in a vertical position, facilitating the release of air bubbles. Optionally, the positioning system 34 also comprises a clamping system of the cable 342 for fixing the position of the same after the rotation of the measuring device 10 and maintaining the groove M' in a vertical position during the sampling time. This clamping system, not illustrated in the figures, is situated on the exterior of the container 30. In the FIGS. 5A and 5B, a positioning system 44 is illustrated, in this occasion in a monitoring system like the one of FIG. 3.

In the figures, an opening and closing mechanism 441 and a cable 442 like the one in FIGS. 4A and 4B are shown.

In both embodiments, upon rotating the device 10 in order to situate its cavity or groove M' in a vertical position, the distance at which the measurements are taken varies slightly: while with the device 10 situated in the insertion position (FIGS. 4A and 5A), this distance was D, with the device 10 rotated and with the cavity M' in vertical position, the distance of the mean point of the cavity M' to the fill line N is D'. It should be noted that what is important is that all the measurements are carried out at a constant depth, whether D or D'.

In addition, the disclosure is not limited to the specific embodiments which have been described, but it also encompasses, for example the variants which can be implemented by the person skilled in the art (for example in terms of the selection of materials, dimensions, components, configuration, etc.).

The invention claimed is:

1. A system for monitoring at least one parameter of a fluid contained in a container, the system comprises:
   a measuring device based on near-infrared spectroscopy configured to be submerged in the cited fluid to be monitored and to take measurements of said fluid, and a flotation system connected to the measuring device,
   wherein said measuring device comprises a first part and a second part, wherein an exterior surface of said first part and an exterior surface of said second part delimit a conduit exterior to the measuring device, said conduit being a measuring area, such that when the measuring device has been submerged in a fluid under supervision, said fluid flows through said conduit,
   said first part comprising a light source working in the visible light and near-infrared spectrum and said second part comprising a detection system based on near-infrared spectroscopy, said light source being configured for illuminating the fluid flowing through said measuring area, and said detection system being configured for taking at least one measurement of the light spectrum which passes through said fluid within the measuring area,
   said flotation system being configured to float on the fluid to be monitored, such that the measuring area of the measuring device is submerged in the fluid at a constant depth with respect to the level of fluid in the container, such that all of the measurements taken by the measuring device are taken at the same depth with respect to the level of the fluid.

2. The system according to claim 1, wherein said monitoring device is connected to said flotation system by means of a bar with a specific length.

3. The system according to claim 1, wherein said flotation system comprises connection means configured for connecting said flotation system to the exterior of the container.

4. The system according to claim 1, wherein said measuring device is configured for taking measurements of the fluid periodically or randomly.

5. The system according to claim 1, wherein said measurement device comprises means for recording the temperature of the fluid to be monitored, means for recording the temperature of the detection system, and means for recording the temperature of the light source.

6. The system according to claim 5, wherein said measuring device comprises processing means configured for processing the measurements taken by the detection system and by said means for recording the temperature of the fluid, means for recording the temperature of the detection system, and said means for recording the temperature of the light source.

7. The system according to claim 1, further comprising a positioning system configured for rotating the measuring device in the interior of the fluid, such that the measuring area is arranged in the interior of the fluid with its opening facing upwards.

8. The system according to claim 7, wherein said positioning system comprises an opening and closing mechanism formed by a first piece and a second piece articulated to each other by means of a common axis, and a cable, wherein said first piece is fixed to the measuring device and said second piece is fixed to the bar, said positioning system being configured for, once the assembly formed by the bar and the measuring device joined by said opening and closing mechanism arranged forming an angle of 90°, is introduced in the container filled with fluid, pulling the cable from the exterior of the container until the opening and closing mechanism is folded forming an angle of 0° between said first and second pieces, the cavity being arranged in a vertical position, facilitating the release of air bubbles.

9. The system according to claim 8, wherein said positioning system further includes a clamping system of the cable configured for fixing the position of the cable following the rotation of the measuring device and for maintaining the groove in a vertical position during the sampling time.

10. The system according to claim 1, wherein said fluid, at least one parameter of which one wishes to monitor, is a wine and said at least one parameter to be monitored is one of the following: the degree of alcohol, the degree of acidity, or the degree of sugars present in the wine.

11. The system according to claim 1, further comprising a container containing a fluid, the measuring device being configured to be submerged in said container.

* * * * *